United States Patent [19]

Gladfelter et al.

[11] 4,413,138

[45] Nov. 1, 1983

[54] GLYCIDYL ETHERS OF AMINOPOLYOLS

[75] Inventors: Elizabeth J. Gladfelter, St. Paul; Edgar R. Rogier, Minnetonka, both of Minn.

[73] Assignee: Henkel Corporation, Minneapolis, Minn.

[21] Appl. No.: 321,969

[22] Filed: Nov. 16, 1981

[51] Int. Cl.³ .................. C07D 303/36; C07D 303/27
[52] U.S. Cl. .................................................... 549/551
[58] Field of Search ......................................... 549/551

[56] References Cited

U.S. PATENT DOCUMENTS 4,328,371  5/1982  Rogier .................................. 564/506

Primary Examiner—Norma S. Milestone
Attorney, Agent, or Firm—Forrest L. Collins

[57] ABSTRACT

The glycidyl ethers of tertiary amino polyols are prepared.

4 Claims, No Drawings

GLYCIDYL ETHERS OF AMINOPOLYOLS

BACKGROUND OF THE INVENTION

1. Field of the Invention

This invention describes compounds containing multiple oxirane groups and a tertiary amine functionality.

2. Description of the Art Practices

It has recently been determined that high molecular weight alcohols may be prepared which are liquid in nature. Such materials are described in the U.S. Pat. No. 4,216,343 dated Aug. 5, 1980 to Rogier. It has also been determined that certain derivatives leading to starting material of the alcohols may be valuably converted to amino alcohols, thereafter to the alkylene oxide adduct of the amino alcohols and then to glycidyl ethers. Such materials are particularly valuable in that they contain oxirane groups on a non-aromatic high molecular weight compound. Moreover tertiary amine functionality in the molecule functions as a catalyst for amine coreactants. It is also noted that the compounds of the present invention are uniquely stable despite the presence of the tertiary amine catalytic group within the molecule.

The novel compounds hereinafter described are conveniently manufactured utilizing phase transfer catalysis. General descriptions of the technology employed in phase transfer catalysis are found in the text, *Phase Transfer Catalysis Principles and Techniques,* Starks and Liotta, Academic Press, New York 178; and in *Phase Transfer Catalysis in Organic Synthesis,* Weber and Gokel, Springer-Verlag.

The starting amino compounds of the present invention are described in U.S. patent application Ser. No. 216,212 filed Dec. 15, 1980 by Rogier. Aromatic N,N-diglycidylamines are known as are non-aromatic cyclic glycidyl compounds.

Percentages and ratios herein are by weight unless otherwise stated and pressures are gauge. Temmperatures are Celsius unless otherwise stated.

SUMMARY OF THE INVENTION

This invention describes glycidyl ethers of tertiary amino polyols of the following structure:

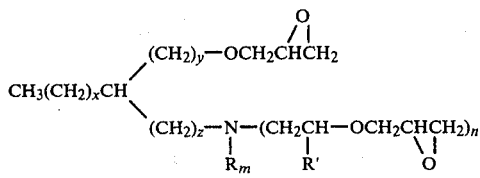

and mixtures thereof; wherein the sum of the non-zero integers x plus y plus z is from 15 through 21; x is greater than or equal to 1; y plus z are greater than or equal to 3; y or z must be 1; n is 1 or 2; m is 0 or 1; and the sum of m plus n is 2; R' is H or $CH_3$; and R is an alkyl group preferably having from 1 through 4 carbon atoms.

DETAILED DESCRIPTION OF THE INVENTION

It will be apparent that more than one starting material may be utilized to obtain the compounds of the present invention. Conveniently, an unsaturated alcohol, such as oleyl alcohol, may be hydroformylated to give a material which has a terminal hydroxyl functionality from the starting alcohol and a formyl group located toward the center of the molecule. A reductive animation is then conducted on such a material utilizing ammonia and hydrogen to convert the formyl group to a primary amine structure. Thereafter, this new primary amine is converted via an alkylene oxide such as ethylene oxide or propylene oxide to the N,N-bis(hydroxyalkyl) substituted amino alcohol.

Thus, starting with oleyl alcohol, one would first obtain 9(10)-formyloctadecanol. This material is then converted through the reductive animation to 9(10)-aminomethyloctadecanol. The 9(10)-aminomethyloctadecanol when reacted with the ethylene oxide gives 9(10)-[N,N-bis(2-hydroxyethyl)]aminomethyloctadecanol. Any unsaturated linear primary alcohol having from 12 to 20 carbon atoms may be utilized to obtain the compounds of the present invention. It is also possible to use polyunsaturated linear primary alcohols, particularly when utilizing cobalt as a catalyst as the hydroformylation reaction has been observed to produce only a monoformyl derivative while reducing any additional unsaturation in the molecule. Thus, linoleyl or linololenyl alcohol yield monoformyloctadecanol which is then derivatized as disclosed above.

An additional starting material which may be utilized to obtain compounds within the scope of the present invention is an unsaturated nitrile such as oleonitrile. In this case, the hydroformylation reaction proceeds with carbon monoxide and hydrogen gas to give 9(10)-formyloctadecanonitrile. This formyl compound is then reduced with hydrogen using a hydrogenation catalyst to give 9(10)-hydroxymethyloctadecylamine. This latter amine is then reacted as described above with ethylene or propylene oxide to give 9(10)-hydroxymethyl-N,N-bis(2-hydroxyalkyl)octadecylamine. Polymers of the alkylene oxide compound are possible which may also be converted to the glycidyl ether.

The compounds described are then reacted with an epihalohydrin compound to obtain the corresponding glycidyl ether. It has also been noted the product would be expected to self-condense upon formation and this is not observed.

In the structural formula given in the Summary, the sum of the integers x plus y plus z is preferably from 16 to 20, and x and y or z are each preferably 2,3,4 or greater within the foregoing constraints. Among the various products of this invention are:

(I) where x is 7(8); y is 9(8); z is 1; n is 2; m is 0; and R' is H.

(II) where x is 7(8); y is 9(8); z is 1; n is 2; m is 0; and R' is methyl (III) where x is 7(8); y is 1; z is 9(8); n is 2; m is 0; and R' is H (IV) where x is 7(8); y is 1; z is 9(8); n is 2; m is 0 and R' is methyl.

The reaction to obtain the glycidyl ether of the present invention is most conveniently done using a phase transfer catalyst.

After the polyhydroxyl compound containing the terminal nitrile has been obtained, the glycidyl ether is obtained. As previously noted, phase transfer catalysis is employed as a preferred method of preparing the glycidyl compounds in the present invention. The glycidylization of the starting compound employs the use of excess amounts of the epihalohydrin. Most conveniently, the epihalohydrin is epichlorohydrin.

The phase transfer catalyst is any one of a numerous group of materials described in the aforementioned texts which are herein incorporated by reference. Examples of suitable catalysts include tetrahexylammonium chloride, benzyl triethylammonium chloride and tetrabutyl ammonium chloride.

When conducting the glycidylization reaction, it is preferred to use sodium hydroxide as the source of alkalinity. The sodium hydroxide may be used conveniently at concentrations of from 20 to 60 percent in an aqueous solution, most conveniently 45 to 55 percent. The general procedure for conducting the glycidyization reaction is to combine the substrate (compound to be glycidylated), the phase transfer catalyst and the aqueous base. It will be noted at this point that the reaction mixture consists of two more or less distinct phases corresponding to the organic and the aqueous layer. The epihalohydrin compound may be added initially or over a period of several hours. Optionally a solvent may be used such as toluene or tetrahydrofuran.

During the addition of the epihalohydrin the reaction temperature should be kept at from about 10 degrees C. to about 80 degrees C., preferably from about 40 degrees C. to about 60 degrees C.

The following are suggested embodiments of the preparation of the compounds of the present invention.

EXAMPLE I

The manufacture of the formyloctadecanol used in the present invention is accomplished by charging a 1 liter Magne Drive, 316 SS autoclave with 606 grams of oleyl alcohol, 3.01 grams of 5 percent rhodium an alumina and 3 grams of triphenylphosphite.

The autoclave is sealed and pressurized to 10 atmospheres with nitrogen under stirring and then vented to atmospheric pressure. The nitrogen purge is repeated twice more to ensure removal of any oxygen present in the autoclave.

The autoclave is then pressurized with premixed carbon monoxide and hydrogen gas in a 1:1 molar ratio to 68 atmospheres at which point heating is started. Stirring is controlled at 1250 rpm and the uptake of the mixture of the gases starts at about 100 degrees C.

The reaction is substantially complete after 4.6 hours and is determined by the cessation of the gas uptake. The confirmation of completeness of the reaction is obtained by sampling the mixture and determining through gas chromatograph analysis that there is less than 1 percent of the starting alcohol in the mixture.

The reaction mixture is cooled to 75 degrees C. vented to atmospheric pressure and purged twice with nitrogen. The contents of the autoclave are discharged at 75 degrees C. under nitrogen pressure through a pressure filter. The yield of the formyloctadecanol is greater than 90 percent.

The reaction may be modified by using triphenylphosphine in place of the triphenylphosphite. The reaction temperature may also be lowered to 90 degrees C. at which point the reaction takes a substantially longer period of time to proceed. As a second alternative, the reaction temperature can be raised to about 150 degrees C. and the reaction time considerably shortened. However, some decomposition of the end product may occur at the higher temperature.

In similar fashion, the mixture of carbon monoxide and hydrogen may be varied as previously described in the Detailed Description of the Invention and may also be varied between about 20 and 500 atmospheres of pressure. The lower end of the pressure range, of course, slows the reaction rate down while the higher pressure condition increases the reaction rate.

EXAMPLE II

9(10)-aminomethyloctadecanol is prepared utilizing the formyloctadecanol of the foregoing example.

Into a one liter 316 SS autoclave equipped with a stirrer, thermocouple and an inlet connected to a positive displacement metering pump are charged 150 grams of absolute ethanol and 30 grams of water-wet Raney nickel.

The autoclave is flushed with nitrogen and sealed. Liquid ammonia in the amount of 150 grams is added to the autoclave using a nitrogen head. The autoclave is then heated to 130 degrees C. resulting in a pressure of 50 atmospheres. The pressure in the system is increased to 61 atmospheres using hydrogen.

The metering pump is then charged with 301 grams of the formylactadecanol obtained from the preceding example. The formyloctadecanol is pumped into the autoclave with stirring over a period of 24 minutes during which time the temperature is controlled to the range of about 128 to 132 degrees C. and the pressure is controlled at from about 57 to about 61 atmospheres. The reaction process is then maintained under the above conditions for an additional two hours after the addition of the formyloctadecanol is complete. The autoclave is then cooled, vented and the product discharged through a filter using nitrogen pressure. The product is stripped of solvent at about 65 degrees C. under a vacuum of less than one torr.

The yield of aminomethylocadecanol is 292 grams having the following analysis. Hydroxyl equivalent weight: 154. Total amine equivalent weight: 351. Secondary plus tertiary amine: 12 meq/kg.

EXAMPLE III

The preparation of 9,(10)-[N,N-bis(2-hydroxyethyl)-]aminomethyloctadecanol is as described below.

A 1 liter autoclave equipped with stirrer, ethylene oxide inlet system, sampling tube and thermocouple is first obtained. Into the autoclave is introduced 452 grams of the aminomethyloctadecanol of Example II.

The autoclave is sealed and flushed with nitrogen three times to exclude oxygen from the reaction mixture. The reaction mass in the autoclave is heated to about 52 degrees and the ethylene oxide is slowly added over a period of approximately 2 hours. The temperature is maintained between 52 and 63 degrees by cooling during the addition of the ethylene oxide. After addition of the ethylene oxide is complete the temperature is maintained at from 54–61 degrees for an additional 1.5 hours.

The reaction vessel is then cooled to 32 degrees and allowed to stand for approximately 16 hours. The reaction is then vented to the atmosphere and the product stripped of volatiles at 70 degrees and less than 1 torr. The yield is observed to be 527 grams having an acetylation equivalent weight of 136 and the total amine equivalent weight of 435. This reaction product corresponds to the theoretical 9,(10)-[N,N-bis(2-hydroxyethyl)]aminomethyloctadecanol.

Shown in Table I on the next page is additional information concerning the preparation of 9(10)-[N,N-bis(2-hydroxyethyl)]aminomethyloctadecanol.

Substantially similar results are obtained when propylene oxide is employed in place of ethylene oxide.

TABLE I
PREPARATION OF 9(10)-[N,N—BIS(2-HYDROXYETHYL)] AMINOMETHYLOCTADECANOL

| AMINO ALCOHOL g (moles) | ETHYLENE OXIDE g (moles) | Temp °C. | Reaction Time (hrs) | Yield (g) | OH Eq Wt | Total |
|---|---|---|---|---|---|---|
| 267(0.89) | 104(2.36) | 39–60 | 10 | 303 | 142 | 462 |
| 454 | 121(2.75) | 45–55 | 8.0 | 546 | 138 | 460 |
| 452 | 121 | 52–63 | 4.0 | 527 | 136 | 435 |
| 438 | 115(2.61) | 45–61 | 5.0 | 523 | 134 | 436 |

EXAMPLE IV

A 50% sodium hydroxide solution (24 grams) is placed in a 100 ml three-neck round bottom flask equipped with a condenser, dropping funnel and nitrogen inlet. The polyol, 9(10)-[N,N-bis(hydroxyethyl)-]aminomethyloctadecanol (9.4 grams), the catalyst tetrabutylammonium chloride (0.28 grams) and epichlorohydrin (13.9 grams) are combined and thereafter added to the aqueous base. The reaction is stirred at 50° C. for 5 hours.

The procedure includes an initial dilution with approximately 100 ml of water. The organic layer is water washed, dried over anhydrous sodium sulfate and analyzed. GCMS gives a m/e of 555; oxirane value of 10.6% of a high epoxy content by infra-red spectrum.

EXAMPLE V

The compounds of this example are prepared by obtaining 9(10)-formyloctadecylnitrile which is reduced per R. Lai* to 9(10)-hydroxymethyloctadecylnitrile using hydrogen and a hydrogenation catalyst (e.g. Ni or Co). The production of 9(10)-hydroxymethyloctadecylamine from the nitrile is then carried out per R. Lai.

*R. Lai: *Obtention of De Derivatives Biofunctionnels,* Rev. Fr. Corps. Gras. 17:455 (1970).b.

The 9(10-hydroxymethyloctadecylamine material is then reacted with two moles of propylene oxide according to the previous examples to obtain 9(10)-hydroxymethyl-N,N-bis(2-hydroxypropyl)octadecylamine. Additional propylene oxide may be used to form higher alkylene oxide condensates.

The glycidyl ether of 9(10)-hydroxymethyl-N,N-bis(2-hydroxypropyl)octadecylamine is obtained as in Example IV.

What is claimed is:

1. The glycidyl ethers of a tertiary amino polyol of the following structure:

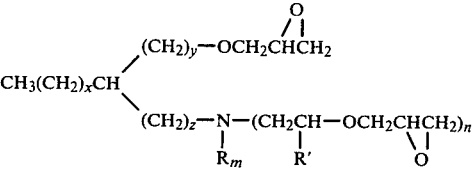

and mixtures thereof; wherein x is 7(8); y is 9(8); z is 1; n is 2; m is 0; and R' is H.

2. The glycidyl ethers of a tertiary amino polyol of the following structure:

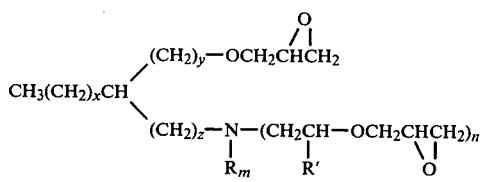

and mixtures thereof; x is 7(8); y is 9(8); z is 1; n is 2; m is 0; and R' is methyl.

3. The glycidyl ethers of a tertiary amino polyol of the following structure:

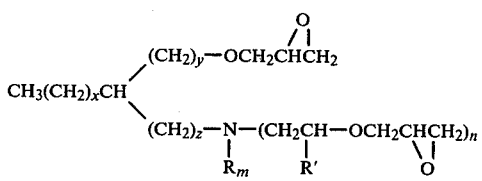

and mixtures thereof; where x is 7(8); y is 1; z is 9(8); n is 2; m is 0; and R' is H.

4. The glycidyl ethers of a tertiary amino polyol of the following structure:

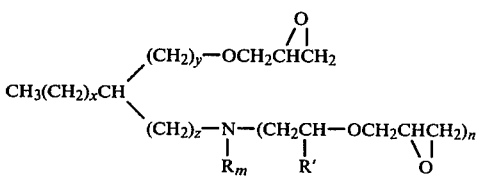

and mixtures thereof; wherein x is 7(8); y is 1; z is 9(8); n is 2; m is 0; and R' is methyl.

* * * * *